United States Patent
Shalaby et al.

(10) Patent No.: US 7,351,426 B2
(45) Date of Patent: Apr. 1, 2008

(54) POLYESTER/CYANOACRYLATE TISSUE ADHESIVE COMPOSITIONS

(75) Inventors: Shalaby W. Shalaby, Anderson, SC (US); M. Aaron Vaughn, Easley, SC (US)

(73) Assignee: Poly-Med, Inc., Anderson, SC (US)

( * ) Notice: Subject to any disclaimer, the term of this patent is extended or adjusted under 35 U.S.C. 154(b) by 878 days.

(21) Appl. No.: 10/792,537

(22) Filed: Mar. 3, 2004

(65) Prior Publication Data

US 2004/0199207 A1 Oct. 7, 2004

Related U.S. Application Data

(60) Continuation-in-part of application No. 09/932,628, filed on Aug. 17, 2001, now Pat. No. 6,723,114, which is a division of application No. 09/439,167, filed on Nov. 12, 1999, now Pat. No. 6,299,631.

(60) Provisional application No. 60/102,868, filed on Nov. 12, 1998, provisional application No. 60/115,836, filed on Jan. 14, 1999.

(51) Int. Cl.
*A61F 13/02* (2006.01)
*A61L 15/16* (2006.01)

(52) U.S. Cl. ............ 424/448; 424/443; 424/445; 424/446; 424/447

(58) Field of Classification Search ............ 424/443, 424/445, 446, 447, 448
See application file for complete search history.

(56) References Cited

U.S. PATENT DOCUMENTS

| | | | |
|---|---|---|---|
| 3,221,745 A | 12/1965 | Coover, Jr. et al. | 128/334 |
| 3,223,083 A | 12/1965 | Cobey | 128/92 |
| 3,264,249 A | 8/1966 | Araki et al. | 260/32.4 |
| 3,559,652 A | 2/1971 | Benitt | 128/334 |
| 4,105,594 A * | 8/1978 | Dieterich et al. | 521/100 |
| 5,350,798 A | 9/1994 | Linden et al. | 525/41 |
| 5,422,068 A | 6/1995 | Shalaby et al. | 422/22 |
| 5,491,198 A | 2/1996 | Shalaby et al. | 525/340 |
| 5,558,517 A | 9/1996 | Shalaby et al. | 433/201.1 |
| 5,612,052 A | 3/1997 | Shalaby | 424/426 |
| 5,624,669 A * | 4/1997 | Leung et al. | 424/78.35 |
| 5,843,124 A * | 12/1998 | Hammerslag | 606/214 |
| 6,299,631 B1 | 10/2001 | Shalaby | 606/214 |
| 6,413,539 B1 | 7/2002 | Shalaby | 424/426 |
| 6,462,169 B1 | 10/2002 | Shalaby | 528/354 |
| 6,467,169 B1 | 10/2002 | Wieres | 29/890 |
| 6,512,023 B1 * | 1/2003 | Malofsky et al. | 523/111 |
| 6,562,936 B1 * | 5/2003 | Hatono et al. | 528/196 |

OTHER PUBLICATIONS

Shalaby, *Encyclopedia of Pharmaceutical Technology*, Swarbrick and Boylan, Eds., Marcel Dekker, Inc., New York, 1988, pp. 465-476.

* cited by examiner

*Primary Examiner*—Helen L Pezzuto
(74) *Attorney, Agent, or Firm*—Leigh P Gregory

(57) ABSTRACT

This invention addresses absorbable cyanoacrylate-based tissue adhesive compositions based primarily on an alkoxy cyanoacrylate combined with one or more alkyl cyanoacrylate(s), a stabilizer against premature anionic polymerization, and/or an absorbable polymeric modifier with improved, and preferably, functional properties for use, primarily, for internal wound repair applications.

14 Claims, No Drawings

POLYESTER/CYANOACRYLATE TISSUE ADHESIVE COMPOSITIONS

This application is a continuation-in-part of U.S. Ser. No. 09/932,628, filed on Aug. 17, 2001, now U.S. Pat. No. 6,723,114 which is a divisional of U.S. Ser. No. 09/439,167, filed on Nov. 12, 1999, now issued as U.S. Pat. No. 6,299,631, which claimed the benefit of prior provisional application U.S. Ser. No. 60/102,868, filed Nov. 12, 1998 and of prior provisional application U.S. Ser. No. 60/115,836, filed Jan. 14, 1999.

BACKGROUND OF THE INVENTION

The prior art on absorbable alkoxyalkyl cyanoacrylate-based tissue adhesives/sealants formulations dealt with polymeric modifiers such as (1) oxalate polymers of triethylene glycol (U.S. Pat. No. 5,350,798); (2) oxalate polymers of polyethylene glycols having an average degree of polymerization in excess of 4 (pending U.S. patent application Ser. No. 09/932,628); and (3) trimethylene carbonate-based polymers (U.S. Pat. No. 6,299,631). The prior art also dealt with stabilized cyanoacrylate-based compositions comprising one or more acidic compound(s) or precursor(s) thereof to maximize the stability of adhesives during storage regardless of the chemical structure of the ester groups (U.S. patent application Ser. No. 10/300,076). All the absorbable tissue adhesive formulations disclosed in the prior art were comprised predominantly of alkoxy cyanoacrylate monomers which are known to undergo absorption in the biologic environment. The presence of the hydrophilic ether linkage in the alkoxyalkyl cyanoacrylate makes them different from all known hydrophobic alkyl cyanoacrylates, in terms of the former superior spreadability on biological tissues. This, in turn, minimizes the required adhesive formulation mass per unit area of treated biological tissues. Meanwhile, certain members of alkyl cyanoacrylate groups can provide a distinctly strong adhesive joint upon anionic polymerization in the biologic environment when used as non-absorbable tissue adhesives. This prompted exploring the option of blending small amounts of one or more alkyl cyanoacrylate(s) with established absorbable tissue adhesive formulations of the prior art to improve the initial adhesive joint strength and allow modulating the retention of the adhesive joint holding strength profile, in vivo, without compromising, significantly, the spreadability of the liquid formulation on biological tissues and the bioabsorption of the polymerized solid products. Accordingly, this invention deals with absorbable tissue adhesive compositions comprising one or more alkoxyalkyl cyanoacrylate-based formulation(s) as a major component and one or more alkyl cyanoacrylate(s) as the minor component of said compositions.

SUMMARY OF THE INVENTION

Thus, the present invention is directed to a cyanoacrylate-based absorbable tissue adhesive composition which includes a blend of at least one alkoxyalkyl cyanoacrylate and at least one alkyl cyanoacrylate, wherein the ratio of alkoxyalkyl cyanoacrylate to alkyl cyanoacrylate is from about 60:40 to about 99:1 by weight. Preferably, the composition further includes more than 2 percent by weight of an absorbable, liquid or amorphous, compliant solid polymeric modifier and less than 0.5 percent by weight of a pyrophosphoric acid stabilizer. In one embodiment the alkoxyalkyl cyanoacrylate is methoxypropyl cyanoacrylate and the alkyl cyanoacrylate is ethyl cyanoacrylate, wherein the methoxypropyl cyanoacrylate to ethyl cyanoacrylate ratio is 7:3 by weight. A composition containing this blend is preferably radiochemically sterilized in a final package for use as an absorbable, sterile tissue adhesive/sealant in repairing internal wounds or redirecting the function of an organ. As such it can be applied to surgically, accidentally, or pathologically compromised skin or internal sites using a delivery device or catheter having covalently linked acidic groups. Such composition is especially suitable for use in wound repairs associated with endoscopic procedures.

In another embodiment the alkoxyalkyl cyanoacrylate is methoxypropyl cyanoacrylate and the alkyl cyanoacrylate is n-butyl cyanoacrylate wherein the methoxypropyl cyanoacrylate to n-butyl cyanoacrylate ratio is 7:3 by weight. In yet another embodiment the alkoxyalkyl cyanoacrylate is methoxypropyl cyanoacrylate and the alkyl cyanoacrylate is iso-butyl cyanoacrylate. In a still further embodiment the alkoxyalkyl cyanoacrylate is methoxypropyl cyanoacrylate and the alkyl cyanoacrylate is an octyl cyanoacrylate. A preferred polymeric modifier is a copolymer of trimethylene carbonate and at least one additional cyclic monomer such as glycolide, lactide, p-dioxanone, 1,5-dioxepan-2-one, or $\epsilon$-caprolactone.

Generally, compositions in accordance with the present invention may be radiochemically sterilized in a final package for use as an absorbable, sterile tissue adhesive/sealant in repairing internal wounds or redirecting the function of an organ. The present invention compositions may also be used in wound repair to provide a modulated adhesive joint strength retention profile.

The present invention is also directed to a radiochemically sterilized absorbable tissue adhesive composition which includes an alkoxyalkyl cyanoacrylate, wherein the composition is irradiated using a radiation dose of about 5 to about 15 kGy.

Accordingly, this invention deals generally with a cyanoacrylate-based absorbable tissue adhesive composition, comprising one or more alkoxy cyanoacrylate(s) at more than 60 weight percent and one or more alkyl cyanoacrylate(s) representing less than 40 weight percent of the total composition. One key aspect of this invention deals with a cyanoacrylate-based tissue adhesive composition comprising one or more alkoxyalkyl cyanoacrylate(s) and one or more alkyl cyanoacrylate(s) as well as more than 2 percent by weight of an absorbable, liquid or amorphous compliant solid polymeric modifier and less than 0.5 percent by weight of pyrophosphoric acid as a stabilizer. It is preferred that the alkoxyalkyl cyanoacrylate is methoxypropyl cyanoacrylate and the alkyl cyanoacrylate is ethyl, propyl, n-butyl, isobutyl, or octyl cyanoacrylate(s). For compositions comprising methoxypropyl cyanoacrylate (MPC) and ethyl cyanoacrylate (EC) or n-butyl (NBC), it is preferred that MPC and EC or NBC are present at a weight ratio of 7:3. Another aspect of this invention deals with a cyanoacrylate-based tissue adhesive composition comprising one or more alkoxyalkyl cyanoacrylate(s) and one or more alkyl cyanoacrylate(s) as well as more than 2 percent by weight of an absorbable, liquid or amorphous, compliant solid polymeric modifier and less than 0.5 percent by weight of pyrophosphoric acid as a stabilizer wherein the polymeric modifier is a copolymer of trimethylene carbonate with one or more cyclic monomer(s) selected from the group represented by glycolide, lactide, p-dioxanone, 1,5-dioxepan-2-one, and $\epsilon$-caprolactone. Another aspect of this invention deals with a cyanoacrylate-based tissue adhesive composition comprising one or more alkoxyalkyl cyanoacrylate(s) and one or more alkyl cyanoacrylate(s) wherein said composition is radiochemically sterilized in the final package for use as an absorbable, sterile tissue adhesive/sealant for repairing internal wounds or redirecting the function of an organ and can be applied to surgically, accidentally, or pathologically compromised skin or internal sites using a delivery device or catheter having covalently linked acidic groups. The use of the tissue adhesive compositions can be associated with endoscopic procedures. Another aspect of this invention deals with a cyanoacrylate-based tissue adhesive composition comprising one or more alkoxyalkyl cyanoacrylate(s) and one or more alkyl cyanoacrylate(s) wherein the said composition is radiochemically sterilized in the final package for use as an absorbable, sterile tissue adhesive/sealant in repairing internal wounds or redirecting the function of an organ. It is preferred that the radiochemically sterilized absorbable tissue adhesive composition comprising an alkoxyalkyl cyanoacrylate using a radiation dose of about 5 to about 15 kGy. Another aspect of this invention deals with a cyanoacrylate-based tissue adhesive composition comprising one or more alkoxyalkyl cyanoacrylate(s) and one or more alkyl cyanoacrylate(s) wherein the said composition is used in wound repair to provide a modulated adhesive joint strength retention profile. Such a profile can be achieved by controlling, primarily, the ratio of the alkoxyalkyl to alkyl cyanoacrylate in the tissue adhesive formulation.

DETAILED DESCRIPTION OF THE PREFERRED EMBODIMENTS

Until recently, practically all the cyanoacrylate-based tissue adhesives were made of a single component of alkyl cyanoacrylate, namely n-butyl, isobutyl, and n-octyl cyanoacrylates. These cyanoacrylates are characterized by being hydrophobic, highly fluid liquids which are clinically used primarily as topical, non-absorbable tissue adhesive as they form strong adhesive joints at repaired tissue sites. However, being non-absorbable limited their clinical use for internal applications in emergency, highly traumatic accidental situations as adhesives/sealants and as blocking agents. The availability of the relatively more hydrophilic alkoxyalkyl cyanoacrylates, which were suspected of being absorbable in the biological environment, led to the development of absorbable alkoxy cyanoacrylate tissue adhesive formulations, which exhibit distinct advantages over their non-absorbable counterparts. These advantages include ease of application during surgical procedures, high compliance of the polymerized formulations, and biomechanical compatibility with soft tissues at the key application sites. Additionally, the broader use of the absorbable tissue adhesives for internal clinical applications signaled a new era in tissue adhesive technology. These new developments, recent advancements in the low-dose radiochemical sterilization technology, better understanding of the degradation and of the absorption mechanisms of tissue adhesive (Transactions of the Society of Biomaterials, 26, 293 and 296, 2003), and a few of the known attributes of the alkyl cyanoacrylates led to the concept of incorporating selected alkyl cyanoacrylate into the established absorbable alkoxyalkyl cyanoacrylate tissue adhesive formulations leading to their surprisingly improved performance as encountered in the present invention. More specifically, this invention illustrates that incorporating small amounts of an alkyl cyanoacrylate, a traditionally acknowledged precursor of a non-absorbable tissue adhesive, results in randomly distributed alkyl cyanoacrylate-derived repeat units in polymeric chains consisting, predominantly, of easily hydrolyzable sequences derived from alkoxyalkyl cyanoacrylate. In effect, as the copolymeric chain undergoes hydrolysis at the alkoxyalkyl ester sequences, the adhesive solubility increases gradually leading to the solid adhesive eventual dissolution and, hence, absorption in the biologic environment, whether or not the alkyl ester sequences remain intact or undergo delayed hydrolysis. And this invention generally deals with absorbable cyanoacrylate-based tissue adhesive compositions based primarily on an alkoxy cyanoacrylate combined with one or more alkyl cyanoacrylate(s), a stabilizer against premature anionic polymerization, and preferably an absorbable polymeric modifier. These compositions are intended to (1) have improved functional properties over tissue adhesives of the prior art for use in wound repair applications, and (2) be useful for new applications that call for modulated adhesive joint strength retention (AJSR) profiles with time at repaired tissues in a manner analogous to that known for absorbable surgical sutures. The AJSR can be modulated, primarily, by controlling the ratio of the alkoxyalkyl to alkyl cyanoacrylate in the adhesive formulation.

One basic aspect of this invention deals with cyanoacrylate-based absorbable tissue adhesive composition comprising one or more alkoxyalkyl cyanoacrylate(s) as a dominant constituent representing at least 60, and preferably 70, and more preferably 80 weight percent of the total composition also containing one or more alkyl cyanoacrylate(s) at less than 40 weight percent and preferably an absorbable polymeric modifier representing more than 2 weight percent of the total composition. One specific aspect of this invention deals with a small amount of acid-generating stabilizer, such as pyrophosphoric acid, to prevent premature anionic polymerization of the formulation upon storage. It is preferred that the stabilizer content does not exceed about 0.5 weight percent of the overall adhesive formulation composition. A specific aspect of this invention deals with a stabilized absorbable tissue adhesive formulation composition made of methoxypropyl cyanoacrylate, ethyl, n-butyl, or isobutyl cyanoacrylates, and an absorbable polymeric modifier at a weight percent of 60 to 80, 20 to 40, and 2 to 10, respectively. It is preferred that the absorbable polymeric modifier in the latter compositions comprises one or more of the polymer(s) made by (1) polymerization of trimethylene carbonate or a mixture of trimethylene carbonate and one or more cyclic monomer(s) selected from the group represented by glycolide, lactide, ε-caprolactone, p-dioxanone, and 1,5-dioxepan-2-one in the presence of a polyaxial initiator such as trimethylol propane; (2) end-grafting a polyalkylene succinate, such as polyethylene or polytrimethylene succinate, with one or more of the following monomer(s): ε-caprolactone, trimethylene, glycolide, lactide, 1,5-dioxapan-2-one, and p-dioxanone; and (3) end-grafting a polyether glycol, such as polyethylene glycol, block copolymers of ethylene and propylene glycol, and random copolymers of ethylene and propylene glycol with one or more monomer(s) selected from the group represented by ε-caprolactone, trimethylene, glycolide, lactide, 1,5-dioxapan-2-one, and p-dioxanone.

Another aspect of the present invention deals with stabilized, sterile cyanoacrylate-based tissue adhesive compositions comprising one or more alkoxyalkyl cyanoacrylate(s) and one or more alkyl cyanoacrylate(s) for use in internal tissue repairs, wherein the sterility is achieved using the radiochemical sterilization scheme described in U.S. Pat. No. 5,422,068 at 5 to 10 kGy radiation dose and preferably at about 5 kGy in the presence of Celcon M-90 as a source of radiolytically generated formaldehyde gaseous sterilant. It is preferred that these radiochemically sterilized, absorbable tissue adhesive compositions be comprised of methoxypropyl cyanoacrylate, an absorbable polymeric modifier, and ethyl or n-butyl cyanoacrylate. It is further preferred that the methoxypropyl cyanoacrylate, the ethyl or n-butyl cyanoacrylates and the polymeric modifier represent 60 to 80, 20 to 40, and 2 to 20 weight percent, respectively of the overall adhesive composition. Another aspect of this invention deals with using the blended tissue adhesives as a wound repair device capable of providing a modulated adhesive joint strength retention profile that can be achieved by controlling, primarily, the ratio of the alkoxyalkyl to the alkyl cyanoacrylate in the formulation. The use of the tissue adhesives for internal applications can include those dealing with repairing internal, accidental and incisional wounds or redirecting the function of an organ. Another aspect of this invention deals with the use of radiochemically or heat sterilized formulations noted above in treating surgically, accidentally, or pathologically compromised skin or internal sites using a delivery device or catheter having covalently linked acid groups such as sulfonic acid groups. Such applications can be associated with endoscopic procedures. Another aspect of this invention relates to incorporating a bioactive agent in the tissue adhesive formulation to mediate the tissue response following the application of said adhesive at the biological site. The bioactive agent can comprise an anti-inflammatory drug.

Additional illustrations of the present invention are provided by the following specific examples.

EXAMPLE 1

Preparation of Absorbable Polyaxial Copolyester Modifier (PAX-CM)

A polyaxial polymeric initiator was first prepared by copolymerization of glycolide (G), ε-caprolactone (CL), and trimethylene carbonate (TMC) at a molar ratio of 5/20/25 in the presence of stannous octoate and trimethyl propane as a catalyst and monomeric initiator, respectively, as described in U.S. Pat. No. 6,462,169. The polyaxial polymeric initiator was then grafted with l-lactide (LL) to yield a segmented, partially crystalline polymer comprising sequences derived from G, CL, TMC, and LL at a ratio of 5/20/25/50. The segmented copolymer was isolated and purified as per U.S. Pat. No. 6,467,169, and then characterized for identity and composition (IR and NMR) molecular weight (GPC) and thermal properties (DSC).

EXAMPLE 2

Preparation of an Absorbable Poly(oxyethylene)oxalate Modifier (POE-OX)

Predried polyethylene glycol 400 (40 g, 0.1 mole) was mixed under dry nitrogen atmosphere with distilled diethyl oxalate (32.1 g, 0.22 mole) and stannous octanoate (275 μL of 0.2 M toluene solution, 0.055 mmole) in a predried glass reactor equipped for mechanical stirring and distillation under atmospheric and reduced pressure. The reaction mixture was heated under nitrogen atmosphere at 150° C. for 6 hours or until the ethanol by-product ceased to distill. Subsequently, the temperature was raised to 185° C. and kept at that temperature for 30 minutes. The temperature was then lowered to 150° C. and predried ethylene glycol (7.44 g, 0.12 mole) was added to the reaction mixture. The reaction was continued at 150° C. for 4 hours or until the ethanol by-product ceased to distill. The temperature was then lowered to room temperature and the reaction mixture was allowed to stir under reduced pressure (about 0.1 m Hg) while heating slowly to 150° C. at such a rate so as to avoid excessive bubbling. The reaction was continued at 150° C. under reduced pressure for 1 hour. The temperature was then raised to 190° C. and the reaction was continued for 3 additional hours. The resulting product was cooled, isolated, characterized for molecular weight (by GPC in dichloromethane), identity (by IR), and composition (by NMR).

EXAMPLE 3

Preparation of 95/5 Methoxypropyl Cyanoacrylate/PAX-CM Control Tissue Adhesive Formulation (CF-1)

In a predried glass reactor equipped for mechanical stirring, PAX-MC (20 g from Example 1) and MPC (20 g) containing a small amount of pyrophosphoric acid (16 mg) were mixed under a dry nitrogen atmosphere. Subsequently, the mixture is then heated to 110° C. and maintained at that temperature until complete mixing is achieved. The mixture was then cooled to 60° C. and an additional amount of MPC (360 g) was added and the mixing continued for about one hour and allowed to cool to room temperature to yield a uniform clear liquid. The product was characterized for identity by infrared and adhesive strength using the fabric peel test [as described by J. D. Kline et al., Sixth World Biomaterials Congress, Trans. Soc. Biomat., III, 1062 (2000)].

EXAMPLE 4

Preparation of 94/6 Methoxypropyl Cyanoacrylate (MPC)/POE-OX Control Tissue Adhesive Formulation (CF-2)

In a predried glass reactor equipped with a mechanical stirrer, POE-OX (20 g from Example 2) and MPC (20 g) containing a small amount of pyrophosphoric acid (20 mg) were mixed under a dry nitrogen atmosphere. The mixture was heated to 110° C. and maintained at that temperature until complete mixing is achieved. The mixture was then cooled to 60° C. and an additional amount of MPC (320 g) was added and the mixing continued for about 1 hour and allowed to cool to room temperature to yield a uniform product. This was characterized for identity by infrared and adhesive strength using the fabric peel test [as described by J. D. Kline et al., Sixth World Biomaterials Congress, Trans. Soc. Biomat., III, 1062 (2000)].

EXAMPLE 5

Preparation of a 70/30 Blend (BL-1) of CF-1 Ethyl Cyanoacrylate

In a predried, two-neck flask equipped for magnetic stirring, CF-1 (70 g) was mixed under a dry nitrogen atmosphere with ethyl cyanoacrylate (30 g) for 30 minutes at room temperature. The resulting blend, BL-1, was isolated and characterized as discussed for CF-1 in Example 3.

EXAMPLE 6

Preparation of a 70/30 Blend (BL-2) of CF-1 and n-Butyl Cyanoacrylate

Blend BL-2 was prepared and characterized using the same experimental scheme as described in Example 5 with the exception of substituting n-butyl cyanoacrylate for ethyl cyanoacrylate.

EXAMPLE 7

General Scheme for Packaging and Sterilizing Absorbable Tissue Adhesive Blends and Their Controls Polyethylene ampoules with tapered nicks were filled under dry nitrogen with aliquots (0.2 ml) of the specific formulation. Eighteen of these ampoules were heat-sealed individually and packaged under dry nitrogen atmosphere in a hermetically sealed secondary package containing a porous, heat-sealed polyester (or polyethylene) pouch containing 200 mg of unstabilized polyformaldehyde powder (Celcon M-90). The secondary package and its contents were radiochemically sterilized using 5 kGy at a dose rate of 32 kGy/hour. The sterilized formulation was tested for identity (by IR), adhesive property (using the fabric peel test as in Example 3), and for sterility. Using standard microbiological assays, the liquid formulation and the surface of the sealed ampoule were tested after more than one month post-irradiation, and were shown to be sterile. The adhesive strength of the sterilized formulation was slightly lower than that of the same formulation before sterilization.

EXAMPLE 8

Comparative Evaluation of Non-Sterile and Radiochemically Sterilized Specimens of Representative Blended Formulations and Controls The testing was conducted using the fabric peel test described in Example 3. Typical results are summarized in Table I.

TABLE I

Comparative Data of Adhesive Joint Strength (AJS) Using The Fabric Peel Test

| Formulations | AJS, N | |
| --- | --- | --- |
| | Non-sterile Specimens | Radiochemically Sterilized Specimens |
| CF-1 | 35 ± 3 | 34 ± 4 |
| BL-1 | 55 ± 5 | 54 ± 5 |
| BL-2 | 43 ± 3 | 41 ± 3 |

Many modifications and variations of this invention can be made without departing from its spirit and scope, as will be apparent to those skilled in the art. The specific embodiments described above are offered by way of example only, and the invention is to be limited only by the terms of the appended claims, along with the full scope of equivalents to which such claims are entitled.

What is claimed is:

1. A cyanoacrylate-based absorbable tissue adhesive composition, comprising a blend of at least one alkoxyalkyl cyanoacrylate and at least one alkyl cyanoacrylate, the ratio of alkoxyalkyl cyanoacrylate to alkyl cyanoacrylate comprising from about 60:40 to about 99:1 by weight, and further comprising greater than 2 percent by weight of a polymeric modifier comprising a copolymer of trimethylene carbonate and at least one additional cyclic monomer selected from the group consisting of glycolide, lactide, p-dioxanone, 1,5-dioxepan-2-one, and ε-caurolactone.

2. A cyanoacrylate-based absorbable tissue adhesive composition as set forth in claim 1 further comprising less than 0.5 percent by weight of a stabilizer comprising pyrophosphoric acid.

3. A cyanoacrylate-based absorbable tissue adhesive composition as set forth in claim 2 wherein the alkoxyalkyl cyanoacrylate comprises methoxypropyl cyanoacrylate and the alkyl cyanoacrylate comprises ethyl cyanoacrylate.

4. A cyanoacrylate-based absorbable tissue adhesive composition as set forth in claim 2 wherein the alkoxyalkyl cyanoacrylate comprises methoxypropyl cyanoacrylate and the alkyl cyanoacrylate comprises n-butyl cyanoacrylate.

5. A cyanoacrylate-based absorbable tissue adhesive composition as set forth in claim 2 wherein the alkoxyalkyl cyanoacrylate comprises methoxypropyl cyanoacrylate and the alkyl cyanoacrylate comprises iso-butyl cyanoacrylate.

6. A cyanoacrylate-based absorbable tissue adhesive composition as set forth in claim 2 wherein the alkoxyalkyl cyanoacrylate comprises methoxypropyl cyanoacrylate and the alkyl cyanoacrylate comprises an octyl cyanoacrylate.

7. A cyanoacrylate-based absorbable tissue adhesive composition as set forth in claim 3 wherein the methoxypropyl cyanoacrylate and ethyl cyanoacrylate are present at a weight ratio of about 7:3.

8. A cyanoacrylate-based absorbable tissue adhesive composition as set forth in claim 7 radiochemically sterilized in a final package for use as an absorbable, sterile tissue adhesive/sealant in repairing internal wounds or redirecting the function of an organ.

9. A cyanoacrylate-based absorbable tissue adhesive composition as set forth in claim 8 that can be applied to surgically, accidentally, or pathologically compromised skin or internal sites using a delivery device or catheter having covalently linked acidic groups.

10. A cyanoacrylate-based absorbable tissue adhesive composition as set forth in claim 9 for use in wound repairs associated with endoscopic procedures.

11. A cyanoacrylate-based absorbable tissue adhesive composition as set forth in claim 4 wherein the methoxypropyl cyanoacrylate and n-butyl cyanoacrylate are present at a weight ratio of 7:3.

12. A cyanoacrylate-based absorbable tissue adhesive composition as set forth in claim 2 radiochemically sterilized in a final package for use as an absorbable, sterile tissue adhesive/sealant in repairing internal wounds or redirecting the function of an organ.

13. A cyanoacrylate-based absorbable tissue adhesive composition as set forth in claim 2 for use in wound repair to provide a modulated adhesive joint strength retention profile.

14. A cyanoacrylate-based absorbable tissue adhesive composition as set forth in claim 1 comprising a radiochemically sterilized absorbable tissue adhesive composition comprising an alkoxyalkyl cyanoacrylate, wherein the composition is irradiated using a radiation dose of about 5 to about 15 kGy.

* * * * *